United States Patent
Minshall et al.

(10) Patent No.: US 9,796,757 B2
(45) Date of Patent: Oct. 24, 2017

(54) COMPOSITIONS AND METHOD FOR TREATING THROMBOSIS

(71) Applicant: The Board of Trustees of the University of Illinois, Urbana, IL (US)

(72) Inventors: Richard D. Minshall, La Grange, IL (US); Luiza Rusu, Antioch, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 57 days.

(21) Appl. No.: 14/784,684

(22) PCT Filed: Apr. 18, 2014

(86) PCT No.: PCT/US2014/034621
§ 371 (c)(1),
(2) Date: Oct. 15, 2015

(87) PCT Pub. No.: WO2014/172618
PCT Pub. Date: Oct. 23, 2014

(65) Prior Publication Data
US 2016/0060293 A1 Mar. 3, 2016

Related U.S. Application Data

(60) Provisional application No. 61/813,915, filed on Apr. 19, 2013.

(51) Int. Cl.
*C07K 7/06* (2006.01)
*A61K 38/00* (2006.01)

(52) U.S. Cl.
CPC .............. *C07K 7/06* (2013.01); *A61K 38/00* (2013.01)

(58) Field of Classification Search
CPC ...................................................... C07K 7/06
See application file for complete search history.

(56) References Cited

U.S. PATENT DOCUMENTS

| | | | | |
|---|---|---|---|---|
| 7,745,391 B2 * | 6/2010 | Mintz | .................... | G06F 19/24 514/19.3 |
| 2004/0031072 A1 * | 2/2004 | La Rosa | .............. | C07K 14/415 800/278 |
| 2007/0044171 A1 * | 2/2007 | Kovalic | ............... | C07K 14/415 800/278 |
| 2011/0195452 A1 * | 8/2011 | Gomord | ............. | C12N 15/8257 435/69.6 |
| 2011/0236314 A1 | 9/2011 | Teo et al. | ........................ | 424/9.1 |
| 2012/0017292 A1 * | 1/2012 | Kovalic | ............... | C07K 14/415 800/260 |

OTHER PUBLICATIONS

Blackmer et al. "G protein βγ directly regulates SNARE protein fusion machinery for secretory granule exocytosis" Nat. Neurosci. 2005 8(4):421-425.

Bonfanti et al. "PADGEM (GMP140) is a component of Weibel-Palade bodies of human endothelial cells" Blood 1989 73(5):1109-1112.
Coughlin, S.J. "Protease-activated receptors in hemostasis, thrombosis and vascular biology" J. Thromb. Haemost. 2005 3(8):1800-1814.
Delaney et al. "The role of Rac1 in glycoprotein Ib-IX-mediated signal transduction and integrin activation" Arterioscler. Thromb. Vasc. Biol. 2012 32(11):2761-2768.
De Meyer et al. "von Willebrand factor: an emerging target in stroke therapy" Stroke 2012 43(2):599-606.
Federici, A.B. & James, P. "Current management of patients with severe von Willebrand disease type 3: a 2012 update" Acta Haematol. 2012 128(2):88-99.
Freynhofer et al. "Prognostic value of plasma von Willebrand factor and its cleaving protease ADAMTS13 in patients with atrial fibrillation" Int. J. Cardiol. 2013 168:317-325.
Fu et al. "Protease-activated receptor-1 activation of endothelial cells induces protein kinase Calpha-dependent phosphorylation of syntaxin 4 and Munc18c: role in signaling p-selectin expression" J. Biol. Chem. 2005 280(5):3178-3184.
Jahn, R. "Principles of exocytosis and membrane fusion" Ann. NY Acad. Sci. 2004 1014:170-178.
Kanaji et al. "Contribution of platelet vs. endothelial VWF to platelet adhesion and hemostasis" J. Thromb. Haemost. 2012 10(8):1646-1652.
Lazzari et al. "Von Willebrand factor (VWF) as a risk factor for bleeding and thrombosis" Hematology 2012 17 Suppl 1:S150-152.
Lenting et al. "von Willebrand factor: the old, the new and the unknown" J. Thromb. Haemost. 2012 10(12):2428-2437.
Levine et al. "Thrombin-mediated release of factor VIII antigen from human umbilical vein endothelial cells in culture" Blood 1982 60(2):531-534.
Lowenstein et al. "Regulation of Weibel-Palade body exocytosis" Trends Cardiovasc. Med. 2005 15(8):302-308.
Matsushita et al. "Nitric oxide regulates exocytosis by S-nitrosylation of N-ethylmaleimide-sensitive factor" Cell 2003 115(2):139-150.
Michiels et al. "Classification and characterization of hereditary types 2A, 2B, 2C, 2D, 2E, 2M, 2N, and 2U (unclassifiable) von Willebrand disease" Clin. Appl. Thromb. Hemost. 2006 12(4):397-420.
Ponimaskin et al. "Acylation of Galpha(13) is important for its interaction with thrombin receptor, transforming activity and actin stress fiber formation" FEBS Lett.1998 429(3):370-374.
Reinders et al. "Isolation of a storage and secretory organelle containing Von Willebrand protein from cultured human endothelial cells" Biochim. Biophys. Acta 1984 804(3):361-369.
Sadler et al. "Update on the pathophysiology and classification of von Willebrand disease: a report of the Subcommittee on von Willebrand Factor" J. Thromb. Haemost. 2006 4(10):2103-2114.
Saini et al. "A family of G protein βγ subunits translocate reversibly from the plasma membrane to endomembranes on receptor activation" J. Biol. Chem.2007 282 (33) :24092-24098.
Sassmann et al. "The Gq/G11-mediated signaling pathway is critical for autocrine potentiation of insulin secretion in mice" J. Clin. Invest. 2010 120(6):2184-2193.
Uemura et al. "Changes in plasma von Willebrand factor and ADAMTS13 levels associated with left atrial remodeling in atrial fibrillation" Thromb. Res. 2009 124(1):28-32.

(Continued)

*Primary Examiner* — Amber D Steele
(74) *Attorney, Agent, or Firm* — Licata & Tyrrell P.C.

(57) ABSTRACT

A peptide, derivative or peptidomimetic that blocks binding of GNA12 to αSNAP is provided as are methods of using the same to inhibit thrombin-induced von Willebrand Factor secretion and prevent or treat thrombosis.

6 Claims, 2 Drawing Sheets

(56) References Cited

OTHER PUBLICATIONS

Vischer, U.M. & Wagner, D.D. "CD63 is a component of Weibel-Palade bodies of human endothelial cells" Blood 1993 82(4):1184-1191.
Weibel, E.R. & Palade, G.E. "New Cytoplasmic Components in Arterial Endothelia" *J. Cell Biol.*1964 23:101-112.
Gabbeta et al. "Platelet signal transduction defect with Gα subunit dysfunction and diminished $G\alpha_q$ in a patient with abnormal platelet responses" PNAS 1997 94:8750-8755.
Rusu et al. "Gα12-dependent constitutive EC-specific vWF secretion" The FASEB Journal 2013 27:878:2.
Rusu et al. "G-protein-dependent basal and evoaked endothelial cell vWF secretion" Blld 2014 123(4):442-450.
International Search Report and Written Opinion in PCT/US2014/034621 dated Oct. 2, 2014.
International Preliminary Report on Patentability in PCT/US2014/034621 dated Oct. 29, 2015.

* cited by examiner

COMPOSITIONS AND METHOD FOR TREATING THROMBOSIS

This application is a U.S. National Stage Application of PCT/US2014/034621 filed Apr. 18, 2014 and claims the benefit of priority of U.S. Provisional Application No. 61/813,915, filed Apr. 19, 2013, the contents of each of which are incorporated herein by reference in their entirety.

This invention was made with government support under contract numbers P01 HL060678 and R01 HL071626 awarded by the National Institutes of Health. The government has certain rights in the invention.

INTRODUCTION

Background von Willebrand factor (vWF) is important for platelet adhesion and subsequent thrombus formation (Delaney, et al. (2012) *Arterioscler. Thromb. Vasc. Biol.* 32(11):2761-2768), therefore, a qualitative or quantitative change in plasma vWF is a predictive factor for cardiovascular disease or bleeding diathesis (Lazzari, et al. (2012) *Hematology* 17 Suppl 1:S150-152). Whereas an elevated plasma level of vWF is associated with increased risk of venous thrombosis, coronary artery disease, and stroke (De Meyer, et al. (2012) *Stroke* 43(2):599-606; Freynhofer, et al. (2013) *Int. J. Cardiol.* 168:317-325; Lenting, et al. (2012) *J. Thromb. Haemost.* 10(12):2428-2437; Uemura, et al. (2009) *Thromb. Res.* 2009 124(1):28-32), inherited or acquired vWF deficiency syndrome (von Willebrand disease, vWD) results in frequent hemorrhagic disorders (Sadler, et al. (2006) *J. Thromb. Haemost.* 4(10):2103-2114). Measurement of vWF continues to be the most important laboratory test for vWD diagnosis (Sadler, et al. (2006) supra). Type 3 vWD, the most severe form due to complete absence of vWF in all vascular compartments including plasma, endothelial cells, and platelets (Federici & James (2012) *Acta Haematol.* 128(2):88-99) is a life-threatening condition due to major defects in coagulation and primary hemostasis.

vWF is stored in Weibel-Palade bodies (WPBs; Reinders, et al. (1984) *Biochim. Biophys. Acta* 804(3):361-369), which are unique secretory granules in endothelial cells (Weibel & Palade (1964) *J. Cell Biol.* 23:101-112) that also contain P-selectin (Bonfanti, et al. (1989) *Blood* 73(5):1109-1112) and other pro-coagulation and pro-inflammatory factors (Vischer & Wagner (1993) *Blood* 82(4):1184-1191). vWF is also stored in and released from platelet α-granules during platelet activation (Kanaji, et al. (2012) *J. Thromb. Haemost.* 10(8):1646-1652). Release of vWF from endothelial cells is thought to be mediated by both constitutive (basal) and agonist-induced signaling pathways, whereas vWF secretion from platelet α-granules is entirely stimulus-induced Lowenstein, et al. (2005) *Trends Cardiovasc. Med.* 15(8):302-308). Circulating vWF levels are likely maintained by basal secretion of vWF from endothelial cells, and thus a change in this process would dramatically affect plasma vWF levels (Michiels, et al. (2006) *Clin. Appl. Thromb. Hemost.* 12(4):397-420). Delivery of endothelial cell-specific vWF to patients and mice with vWD is sufficient to correct defects in hemostasis (Sadler, et al. (2006) supra; Kanaji, et al. (2012) supra), whereas platelet-derived vWF only partially restores defects in thrombosis (Kanaji, et al. (2012) supra).

Exocytosis, mediated by fusion of secretory vesicles with the plasma membrane (Jahn (2004) *Ann. NY Acad. Sci.* 1014:170-178), requires the ATPase N-ethylmaleimide-sensitive-fusion factor (NSF), soluble NSF attachment protein alpha (α-SNAP), and SNAP receptors (SNAREs) (Lowenstein, et al. (2005) supra; Matsushita, et al. (2003) *Cell* 115(2):139-150). α-SNAP binding to the cis-SNARE complex in the fused membrane mediates recruitment of NSF that together promote exocytosis and SNARE disassembly (Lowenstein, et al. (2005) supra). Although this core secretory machinery is widely expressed, there is significant heterogeneity in the signaling mechanisms that control endothelial secretory granule exocytosis (Fu, et al. (2005) *J. Biol. Chem.* 280(5):3178-3184).

Activation of G protein-coupled receptors (GPCRs) and G protein α subunits (Gs, Gi and Gq/11) can stimulate secretory granule release (Sassmann, et al. (2010) *J. Clin. Invest.* 120(6):2184-2193). Thrombin (enzyme IIa) produced during vascular injury activates the coagulation cascade and also potentiates vWF secretion via stimulation of protease activated receptor-1 (PAR1)-dependent signaling (Levine, et al. (1982) *Blood* 60(2):531-534; Coughlin (2005) *J. Thromb. Haemost.* 3(8):1800-1814). The general mechanism by which G protein α subunits regulate exocytosis is not known, although it has been suggested G proteins mediate cell-type and compartment-specific functions and early transport events (Sassmann, et al. (2010) supra). Direct G protein-dependent regulation of the SNARE protein fusion machinery required for secretory granule exocytosis has been reported (Blackmer, et al. (2005) *Nat. Neurosci.* 8(4):421-425). Further, distinct from their traditional plasma membrane localization (Ponimaskin, et al. (1998) *FEBS Lett.* 429(3):370-374), heterotrimeric G proteins have been shown to shuttle rapidly between plasma membrane and intracellular membranes where they have distinct roles on specific organelles, including those in exocytotic pathways (Chisari, et al. (2007) *J. Biol. Chem.* 282(33):24092-24098).

SUMMARY OF THE INVENTION

The present invention is a peptide, e.g., a peptide of less than 50 amino acid residues in length, having the sequence Arg-Cys-Leu-Leu-Pro-Ala (SEQ ID NO:1), or a derivative or peptidomimetic thereof. In one embodiment, the derivative includes a post-translation modification selected from the group of acetylation, amidation, formylation, hydroxylation, methylation, myristoylation, phosphorylation, sulfatation, glycosylation, and lipidation. A pharmaceutical composition and methods for using the peptide, derivative or peptidomimetic to inhibit thrombin-induced von Willebrand Factor secretion and prevent or treat thrombosis are also provided.

BRIEF DESCRIPTION OF THE DRAWINGS

FIGS. 3A-3C show the effect of Gα12 and Myr-SBD on vWF secretion and mortality associated with CLP/sepsis in rodent models. FIG. 3A. Time course of plasma vWF levels (mean±SD; n=4) after CLP-induced fulminant sepsis in WT Sprague-Dawley rats; p<0.05 vs. time 0. FIG. 3B. Myr-SBD peptide administered i.v. at the time of CLP or SHAM surgery in mice reduced plasma vWF measured at 24 hours compared to Myr-Scr treated CLP mice (n=3/group). FIG. 3C. CLP vs. SHAM surgery in WT and Gα12$^{-/-}$ mice (n=3/group) revealed 3/3 Gα12$^{-/-}$ mice survived CLP whereas 3/3 C57BL/6 WT mice died within 96 hours.

DETAILED DESCRIPTION OF THE INVENTION

It has now been shown that vWF release is dependent on Gα12 and Gαq/11 signaling via RhoA- and Ca$^{2+}$/α-SNAP-dependent mobilization and fusion of WPBs. In addition, a direct interaction of Gα12 with α-SNAP has been found to serve as a catalyst for basal vWF secretion. Experiments employing an isolated perfused mouse lung model demonstrated decreased basal EC-specific vWF release in Gα12$^{-/-}$ mice as compared to WT, Gα11$^{-/-}$, and EC-Gαq$^{-/-}$; Gα11$^{-/-}$ mice. Following stimulation of pulmonary vascular endothelial cells with a PAR1 activating peptide, significantly less vWF release was observed from Gα12$^{-/-}$ and EC-Gαq$^{-/-}$; Gα11$^{-/-}$ mouse lung ECs compared with WT mice. Mice lacking Gα12 displayed low plasma levels of vWF which correlated well with defective exocytosis of vWF from WPBs in the absence of Gα12. Furthermore, mice with Gα12 deficiency alone exhibited reduced platelet thrombus formation following laser injury to the isolated cremaster artery, as well as reduced flow-dependent adhesion of platelets on vWF strings in vitro. These functional defects were shown to be due to impaired secretion and low plasma vWF level in absence of Gα12, rather than to abnormal vWF multimerization.

Based upon the identification of G protein-dependent regulatory mechanism of basal (constitutive) and evoked EC vWF secretion, a six amino acid GNA12-derived peptide was generated (Arg-Cys-Leu-Leu-Pro-Ala; SEQ ID NO:1) that blocks binding of GNA12 to αSNAP thereby reducing the level of vWF secretion in circulation without altering the activity of GNA12 or downstream effector molecules. This peptide, generally referred to herein as an αSNAP-binding domain or SBD peptide, as well as derivatives and mimetics thereof are of use in preventing, mitigating, attenuating or treating diseases or conditions mediated by platelet aggregation.

Accordingly, the present invention provides a peptide that prevents or inhibits vWF secretion from cells. As used herein, a "peptide" refers to a molecule at least two amino acids covalently linked by an amide bond. In particular embodiments, the peptide of the invention is the SBD peptide Arg-Cys-Leu-Leu-Pro-Ala (SEQ ID NO:1). In some embodiments, the SBD peptide has the sequence of SEQ ID NO:1, however, SBD peptide derivatives and mimetics are also within the scope of the invention.

As used herein, a peptide derivative is a molecule which retains the primary amino acids of the peptide, however, the N-terminus, C-terminus, and/or one or more of the side chains of the amino acids therein have been chemically altered or derivatized. Such derivatized peptides include, for example, naturally occurring amino acid derivatives, for example, 4-hydroxyproline for proline, 5-hydroxylysine for lysine, homoserine for serine, ornithine for lysine, and the like. Other derivatives or modifications include, e.g., a label, such as fluorescein or tetramethylrhodamine; or one or more post-translational modifications such as acetylation, amidation, formylation, hydroxylation, methylation, myristoylation, phosphorylation, sulfatation, glycosylation, or lipidation. Indeed, certain chemical modifications, in particular N-terminal glycosylation, have been shown to increase the stability of peptides in human serum (Powell et al. (1993) *Pharma. Res.* 10:1268-1273). Peptide derivatives also include those with increased membrane permeability obtained by N-myristoylation (Myr) (Brand, et al. (1996) *Am. J. Physiol. Cell. Physiol.* 270:C1362-C1369). An exemplary peptide derivative is Myr-Arg-Cys-Leu-Leu-Pro-Ala (SEQ ID NO:2).

In addition, a peptide derivative of the invention can include a cell-penetrating sequence which facilitates, enhances, or increases the transmembrane transport or intracellular delivery of the peptide into a cell. For example, a variety of proteins, including the HIV-1 Tat transcription factor, *Drosophila* Antennapedia transcription factor, as well as the herpes simplex virus VP22 protein have been shown to facilitate transport of proteins into the cell (Wadia and Dowdy (2002) *Curr. Opin. Biotechnol.* 13:52-56). Further, an arginine-rich peptide (Futaki (2002) *Int. J. Pharm.* 245: 1-7), a polylysine peptide containing Tat PTD (Hashida, et al. (2004) *Br. J. Cancer* 90(6):1252-8), Pep-1 (Deshayes, et al. (2004) *Biochemistry* 43(6):1449-57) or an HSP70 protein or fragment thereof (WO 00/31113) is suitable for enhancing intracellular delivery of a peptide or peptidomimetic of the invention into the cell.

While a peptide of the invention can be derivatized with by one of the above indicated modifications, it is understood that a peptide of this invention may contain more than one of the above described modifications within the same peptide.

As indicated, this invention also encompasses peptidomimetics of the peptides disclosed herein. Peptidomimetics refer to a synthetic chemical compound which has substantially the same structural and/or functional characteristics of the peptides of the invention. The mimetic can be entirely composed of synthetic, non-natural amino acid analogues, or can be a chimeric molecule including one or more natural peptide amino acids and one or more non-natural amino acid analogs. The mimetic can also incorporate any number of natural amino acid conservative substitutions as long as such substitutions do not destroy the activity of the mimetic. Routine testing can be used to determine whether a mimetic has the requisite activity, e.g., that it can inhibit binding of GNA12 to αSNAP. The phrase "substantially the same," when used in reference to a mimetic or peptidomimetic, means that the mimetic or peptidomimetic has one or more activities or functions of the referenced molecule, e.g., reducing the level of vWF secretion in circulation without altering the activity of GNA12 or downstream effector molecules.

There are advantages for using a mimetic of a given peptide. For example, there are cost savings and improved patient compliance associated with peptidomimetics, since they can be administered orally compared with parenteral administration for peptides. Furthermore, peptidomimetics are cheaper to produce than peptides.

Thus, peptides described above have utility in the development of such small chemical compounds with similar biological activities and therefore with similar therapeutic utilities. The techniques of developing peptidomimetics are conventional. For example, peptide bonds can be replaced by non-peptide bonds or non-natural amino acids that allow the peptidomimetic to adopt a similar structure, and therefore biological activity, to the original peptide. Further modifications can also be made by replacing chemical groups of the amino acids with other chemical groups of similar structure. The development of peptidomimetics can be aided by determining the tertiary structure of the original peptide, either free or bound to the target protein, by NMR spectroscopy, crystallography and/or computer-aided molecular modeling. These techniques aid in the development of novel compositions of higher potency and/or greater bioavailability and/or greater stability than the original peptide (Dean (1994) *BioEssays* 16:683-687; Cohen & Shatzmiller (1993) *J. Mol. Graph.* 11:166-173; Wiley & Rich (1993) *Med. Res. Rev.* 13:327-384; Moore (1994) *Trends Pharmacol. Sci.* 15:124-129; Hruby (1993) *Biopolymers* 33:1073-1082; Bugg, et al. (1993) *Sci. Am.* 269:92-98). Once a potential peptidomimetic compound is identified, it may be synthesized and assayed using an assay described herein or any other appropriate assay for monitoring vWF secretion.

It will be readily apparent to one skilled in the art that a peptidomimetic can be generated from a peptide described herein. It will furthermore be apparent that the peptidomimetic of this invention can be further used for the development of even more potent non-peptidic compounds, in addition to their utility as therapeutic compounds.

Peptidomimetic compositions can contain any combination of non-natural structural components, which are typically from three structural groups: residue linkage groups other than the natural amide bond ("peptide bond") linkages; non-natural residues in place of naturally occurring amino acid residues; residues which induce secondary structural mimicry, i.e., induce or stabilize a secondary structure, e.g., a beta turn, gamma turn, beta sheet, alpha helix conformation, and the like; or other changes which confer resistance to proteolysis. For example, a peptide can be characterized as a mimetic when one or more of the residues are joined by chemical means other than an amide bond. Individual peptidomimetic residues can be joined by amide bonds, non-natural and non-amide chemical bonds other chemical bonds or coupling means including, for example, glutaraldehyde, N-hydroxysuccinimide esters, bifunctional maleimides, N,N'-dicyclohexylcarbodiimide (DCC) or N,N'-diisopropylcarbodiimide (DIC). Linking groups alternative to the amide bond include, for example, ketomethylene (e.g., —C(=O)—$CH_2$— for —C(=O)—NH—), aminomethylene ($CH_2$—NH), ethylene, olefin (CH=CH), ether ($CH_2$—O), thioether ($CH_2$—S), tetrazole ($CN_4$—), thiazole, retroamide, thioamide, or ester (see, e.g., Spatola (1983) in *Chemistry and Biochemistry of Amino Acids, Peptides and Proteins*, 7:267-357, "Peptide and Backbone Modifications," Marcel Decker, NY).

As discussed, a peptide can be characterized as a mimetic by containing one or more non-natural residues in place of a naturally occurring amino acid residue. Non-natural residues are known in the art. Particular non-limiting examples of non-natural residues useful as mimetics of natural amino acid residues are mimetics of aromatic amino acids include, for example, D- or L-naphylalanine; D- or L-phenylglycine; D- or L-2 thieneylalanine; D- or L-1, -2, 3-, or 4-pyreneylalanine; D- or L-3 thieneylalanine; D- or L-(2-pyridinyl)-alanine; D- or L-(3-pyridinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-p-fluoro-phenylalanine; D- or L-p-biphenylphenylalanine; D- or L-p-methoxy-biphenyl-phenylalanine; and D- or L-2-indole(alkyl)alanines, where alkyl can be substituted or unsubstituted methyl, ethyl, propyl, hexyl, butyl, pentyl, isopropyl, iso-butyl, sec-isotyl, iso-pentyl, or a non-acidic amino acid. Aromatic rings of a non-natural amino acid that can be used in place a natural aromatic ring include, for example, thiazolyl, thiophenyl, pyrazolyl, benzimidazolyl, naphthyl, furanyl, pyrrolyl, and pyridyl aromatic rings.

Cyclic peptides or cyclized residue side chains also decrease susceptibility of a peptide to proteolysis by exopeptidases or endopeptidases. Thus, certain embodiments embrace a peptidomimetic of the peptide disclosed herein, whereby one or more amino acid residue side chains are cyclized according to conventional methods.

Mimetics of acidic amino acids can be generated by substitution with non-carboxylate amino acids while maintaining a negative charge; (phosphono)alanine; and sulfated threonine. Carboxyl side groups (e.g., aspartyl or glutamyl) can also be selectively modified by reaction with carbodiimides (R'—N—C—N—R') including, for example, 1-cyclohexyl-3(2-morpholinyl-(4-ethyl) carbodiimide or 1-ethyl-3(4-azonia-4,4-dimetholpentyl) carbodiimide. Aspartyl or glutamyl groups can also be converted to asparaginyl and glutaminyl groups by reaction with ammonium ions.

Lysine mimetics can be generated (and amino terminal residues can be altered) by reacting lysinyl with succinic or other carboxylic acid anhydrides. Lysine and other alpha-amino-containing residue mimetics can also be generated by reaction with imidoesters, such as methyl picolinimidate, pyridoxal phosphate, pyridoxal, chloroborohydride, trinitrobenzenesulfonic acid, O-methylisourea, 2,4, pentanedione, and transamidase-catalyzed reactions with glyoxylate.

Methionine mimetics can be generated by reaction with methionine sulfoxide. Proline mimetics of include, for example, pipecolic acid, thiazolidine carboxylic acid, dehydroproline, 3- or 4-methylproline, and 3,3,-dimethylproline.

One or more residues can also be replaced by an amino acid (or peptidomimetic residue) of the opposite chirality. Thus, any amino acid naturally occurring in the L-configuration (which can also be referred to as R or S, depending upon the structure of the chemical entity) can be replaced with the same amino acid or a mimetic, but of the opposite chirality, referred to as the D-amino acid, but which can additionally be referred to as the R- or S-form. As will be appreciated by one skilled in the art, the peptidomimetics of the present invention can also include one or more of the modifications described herein for derivatized peptides, e.g., a label, one or more post-translational modifications, or cell-penetrating sequence.

In certain embodiments, the size of a peptide, derivative or peptidomimetic of the invention is 5, 6, 7, 8, 9, 10, 11, 12, 13, 14, 15 or up to 50 amino acid residues, including all ranges derivable therein. It is contemplated that peptides may be modified by truncation, rendering them shorter than their corresponding parent form, but also they might be altered by fusing or conjugating a heterologous protein sequence with a particular function (e.g., for targeting, localization, or purification purposes, etc.).

Desirably, peptides, derivatives and peptidomimetics of this invention have a sequence that is substantially identical to SEQ ID NO:1. The term "substantially identical" is used herein to mean that the sequence has at least 75% or more identity to a reference sequence (e.g., 80%, 85%, 90%, 95%, 96%, 97%, 98%, 99%). The length of comparison sequences will generally be at least 5 amino acids. In one aspect, the identity is over a defined sequence region, e.g., the amino or carboxy terminal 3 to 5 residues.

The peptides, derivatives and peptidomimetics can be produced and isolated using any method known in the art. Peptides can be synthesized, in whole or in part, using chemical methods known in the art (see, e.g., Caruthers (1980) *Nucleic Acids Res. Symp. Ser.* 215-223; Horn (1980) *Nucleic Acids Res. Symp. Ser.* 225-232; and Banga (1995)

*Therapeutic Peptides and Proteins, Formulation, Processing and Delivery Systems*, Technomic Publishing Co., Lancaster, Pa.). Peptide synthesis can be performed using various solid-phase techniques (see, e.g., Roberge (1995) *Science* 269:202; Merrifield (1997) *Methods Enzymol.* 289:3-13) and automated synthesis may be achieved, e.g., using the ABI 431A Peptide Synthesizer (Perkin Elmer) in accordance with the manufacturer's instructions.

Individual synthetic residues and peptides incorporating mimetics can be synthesized using a variety of procedures and methodologies known in the art (see, e.g., *Organic Syntheses Collective Volumes*, Gilman, et al. (Eds) John Wiley & Sons, Inc., NY). Peptides and peptide mimetics can also be synthesized using combinatorial methodologies. Techniques for generating peptide and peptidomimetic libraries are well-known, and include, for example, multipin, tea bag, and split-couple-mix techniques (see, for example, al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; and Ostresh (1996) *Methods Enzymol.* 267:220-234). Modified peptides can be further produced by chemical modification methods (see, for example, Belousov (1997) *Nucleic Acids Res.* 25:3440-3444; Frenkel (1995) *Free Radic. Biol. Med.* 19:373-380; and Blommers (1994) *Biochemistry* 33:7886-7896).

Alternatively, peptides of this invention can be prepared in recombinant protein systems using polynucleotide sequences encoding the peptides. By way of illustration, a nucleic acid molecule encoding a peptide of the invention is introduced into a host cell, such as bacteria, yeast or mammalian cell, under conditions suitable for expression of the peptide, and the peptide is purified or isolated using methods known in the art. See, e.g., Deutscher et al. (1990) *Guide to Protein Purification: Methods in Enzymology* Vol. 182, Academic Press.

It is contemplated that the peptide disclosed herein can be used as a lead compound for the design and synthesis of compounds with improved efficacy, clearance, half-lives, and the like. One approach includes structure-activity relationship (SAR) analysis (e.g., NMR analysis) to determine specific binding interactions between the compound and target protein to facilitate the development of more efficacious agents. Agents identified in such SAR analysis or from agent libraries can then be screened for their ability to reduce the level of vWF secretion.

Peptides, derivatives, and peptidomimetics of this invention find application in blocking binding of GNA12 to αSNAP without altering the activity of GNA12, reducing the level of vWF secretion in circulation, and preventing, mitigating, attenuating or treating diseases or conditions mediated by platelet aggregation. Thus, methods for reducing vWF secretion and preventing or treating disease are also provided by this invention.

In accordance with present invention, the secretion of vWF is reduced or decreased by contacting a cell, in particular a vascular endothelial cell, with a peptide, derivative or peptidomimetic of this invention that blocks binding of GNA12 to αSNAP so that secretion of vWF is reduced or decreased. Desirably, the peptide, derivative or peptidomimetic is administered in an amount that effectively reduced or decreased the amount of secreted vWF by at least 60%, 70%, 80%, 90%, 95%, 99% or 100% as compared to cells not contacted with the peptide, derivative or peptidomimetic. It is contemplated that this method of the invention can be used to reduce secretion of vWF in a human subject (i.e., in vivo) as well as in an isolated cell or cell culture (i.e., in vitro).

In another embodiment, a subject is treated with one or more peptides, derivatives or peptidomimetics of this invention of the invention in the treatment of a disease or condition. Such compositions may be administered to a vertebrate, preferably a mammal, and more preferably a human. The terms "patient" and "subject" are used interchangeably throughout the specification, and these terms include both human and veterinary subjects.

The peptide, derivative or peptidomimetic provided herein is administered to a subject in an amount effective to inhibit, reduce, block or otherwise modulate vWF-mediated platelet adhesion, activation and/or aggregation. The peptide, derivative or peptidomimetic may be administered by numerous routes of administration. Such routes of administration include, but are not limited to, oral routes; topical routes, such as intranasally, vaginally or rectally; parenteral routes such as intravenous, subcutaneous, intradermal, intramuscular, intraarticular, intraperitoneal, intracerebral, intracerebroventricular, intra-ocular, intraarterial, intraportal, intralesional and intrathecal administration, or by sustained release systems or by implantation devices. Suitable routes of administration may also be used in combination, such as intravenous administration followed by subcutaneous administration. The route of administration, however, is determined by the attending physician.

Oral dosage forms may be administered as tablets, capsules, pills, powders, granules, elixirs, tinctures, suspensions, syrups or emulsions. Topical dosage forms include creams, ointments, lotions, aerosol sprays and gels for intranasal vehicles, inhalants or transdermal patches. When parenteral administration is contemplated, the pharmaceutical compositions for use in this invention may be in the form of a pyrogen-free, parenterally acceptable aqueous solution containing the active agent in a pharmaceutically acceptable vehicle. A particularly suitable vehicle for parenteral injection is sterile distilled water in active agent is formulated as a sterile, isotonic solution, appropriately preserved. Preparation can involve the formulation of the active agent with, e.g., injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired active agent. The compositions may also be formulated for inhalation. In these embodiments, a peptide of the invention is formulated as a dry powder for inhalation, or inhalation solutions may also be formulated with a propellant for aerosol delivery, such as by nebulization. Pulmonary administration is further described in PCT/US94/001875, which describes pulmonary delivery of chemically modified proteins.

The dosage regimen utilizing the peptide, derivative or peptidomimetic of this invention is selected in accordance with a variety of factors including type, species, age, weight, sex and medical condition of the patient; the severity of the condition to be treated; the route of administration; the renal and hepatic function of the patient; and the particular active agent or salt thereof employed. An ordinarily skilled physician or veterinarian can readily determine and prescribe the effective amount of the drug required to prevent, counter or arrest the progress of the condition.

High blood vWF levels, occurring either by pathologic increase in the rate of constitutive vWF secretion or by increased evoked vWF release by dysfunctional, activated endothelial cells, is a risk factor for disseminated coagulation in thrombo-embolic and inflammatory/septic conditions. The ability to block vWF release from endothelial cells provides direct anti-thrombotic therapy via inhibition of constitutive and evoked (e.g., induced by thrombin) vWF release from WPBs. Accordingly, the peptide, derivative, or peptidomimetic of this invention is of use in preventing or treating thrombosis associated with a variety of disease conditions.

In one embodiment, a peptide, derivative, or peptidomimetic is administered as a therapy or prophylaxis to prevent a primary and/or secondary ischemic event, such as angina, reocclusion after percutaneous transluminal coronary angioplasty, restenosis, thrombotic stroke, transient ischemic attack, reversible ischemic neurological deficit, myocardial infarction or intermittent claudication. Thus, in some embodiments, a subject being treated by the instant methods is a subject at risk for an ischemic event such as a subject having arterial sclerosis, a subject having suffered from a previous ischemic event or a subject with a family history of ischemic events.

In another embodiment, a peptide, derivative, peptidomimetic, or combination thereof is administered to a subject having a blood clot in an amount sufficient to reduce the size or mass of the blood clot. For example, a peptide, derivative, or peptidomimetic is used in the treatment (prevention) of pulmonary embolism, venous thrombosis, deep vein thrombosis, portal vein thrombosis, renal vein thrombosis, jugular vein thrombosis, Budd-Chiari syndrome, Paget-Schroetter disease, cerebral venous sinus thrombosis, arterial thrombosis, thrombotic stroke, myocardial infarction or ministrokes. The peptide, derivative, or peptidomimetic is also useful to prevent clots in transplant and to mitigate the risk of future strokes in subjects at risk of strokes.

A peptide, derivative, peptidomimetic of this invention, or combination thereof, is also useful for treating disseminated intravascular coagulation (DIC), also known as disseminated intravascular coagulopathy or less commonly as consumptive coagulopathy, a pathological activation of coagulation (blood clotting) mechanisms that happens in response to a variety of diseases. DIC leads to the formation of small blood clots inside the blood vessels throughout the body. As the small clots consume coagulation proteins and platelets, normal coagulation is disrupted and abnormal bleeding occurs from the skin (e.g., from sites where blood samples have been taken), the gastrointestinal tract, the respiratory tract and surgical wounds. The small clots also disrupt normal blood flow to organs (such as the kidneys), which may malfunction as a result. DIC can occur acutely but also on a slower, chronic basis, depending on the underlying problem. It is common in the critically ill, and may participate in the development of multiple organ failure, which may lead to death. Sepsis can lead to this DIC condition.

The peptide, derivative, peptidomimetic, or combination thereof is also of use in the treatment of a variety of other vWF-mediated diseases and disorders, including cardiovascular, thrombotic and hematologic diseases and disorders involving vWF-mediated platelet adhesion, activation and/or aggregation. Diseases and disorders to be treated, prevented or ameliorated particularly include essential thrombocytopenia, hemolytic uremic syndrome, thrombotic thrombocytopenic purpura (TTP), familial TTP, secondary TTP, idiopathic TTP, congenital TTP, Type 2b von Willebrand's Disease, pseudo type 2b von Willebrand's Disease, peripheral artery disease, peripheral arterial occlusive disease, atrial fibrillation, carotid stenosis, unstable carotid disease, unstable carotid lesions, and thrombotic microangiopathy during sepsis.

"Treating" a mammal having a disease or disorder means accomplishing one or more of the following: reducing the severity of the disease; arresting the development of the disease or disorder; inhibiting worsening of the disease or disorder; limiting or preventing recurrence of the disease or disorder in patients that have previously had the disease or disorder; causing regression of the disease or disorder; improving or eliminating the symptoms of the disease or disorder; and/or improving survival.

As used herein, the term "amount effective," "effective amount" or "therapeutically effective amount" refers to an amount of the peptide of the invention or a pharmaceutical composition containing the inventive peptide sufficient to achieve the stated desired result, for example, treating or limiting development of thrombosis. The amount of the peptide which constitutes an effective amount or therapeutically effective amount may vary depending on the severity of the disease, the condition, weight, or age of the patient to be treated, the frequency of dosing, or the route of administration, but can be determined routinely by one of ordinary skill in the art. A clinician may titer the dosage or route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 100 mg/kg, or 1 µg/kg up to about 100 mg/kg, or 5 µg/kg up to about 100 mg/kg.

The peptide, derivative or peptidomimetic may be administered prior to, during and/or after a medical procedure. For example, a pharmaceutical composition containing a peptide, derivative or peptidomimetic may be administered in conjunction (before, during and/or after) with medical procedures, such as carotid endarterectomy, carotid stenting, carotid angioplasty with or without stenting, medical management of a patient with symptomatic or asymptomatic carotid stenosis, CABG surgery, percutaneous coronary intervention and heart valve replacement. The pharmaceutical compositions may also be administered in conjunction (before, during and/or after) with other medical procedures, such as dialysis or hemodialysis.

Successful clinical use of a peptide, derivative or peptidomimetic of the invention can be determined by the skilled clinician based upon routine clinical practice, e.g., by monitoring frequency of respiratory infections and/or coughing; or changes in breathing, abdominal pain, appetite, and/or growth according to methods known in the art.

Agents disclosed herein can be employed as isolated molecules (i.e., isolated peptides, derivatives, or peptidomimetics), administered in conventional pharmaceutical compositions or in the case of peptides, be expressed from nucleic acids encoding said peptides. Such nucleic acids can, if desired, be naked or be in a carrier suitable for passing through a cell membrane (e.g., DNA-liposome complex), contained in a vector (e.g., plasmid, retroviral vector, lentiviral, adenoviral or adeno-associated viral vectors and the like), or linked to inert beads or other heterologous domains (e.g., antibodies, biotin, streptavidin, lectins, etc.), or other appropriate compositions. Thus, both viral and non-viral means of nucleic acid delivery can be achieved and are contemplated. Desirably, a vector used in accordance with the invention provides all the necessary control sequences to facilitate expression of the peptide. Such expression control sequences can include but are not limited to promoter sequences, enhancer sequences, etc. Such expression control sequences, vectors and the like are well-known and routinely employed by those skilled in the art.

For example, when using adenovirus expression vectors, the nucleic acid molecule encoding a peptide can be ligated to an adenovirus transcription/translation control complex, e.g., the late promoter and tripartite leader sequence. Alternatively, the vaccinia virus 7.5K promoter can be used. (see e.g., Mackett, et al. (1982) Proc. Nati. Acad. Sci. USA 79:7415-7419; Mackett, et al. (1984) J. Virol. 49:857-864; Panicali, et al. (1982) Proc. Natl. Acad. Sci. USA 79:4927-4931). Mammalian expression systems further include vectors specifically designed for "gene therapy" methods including adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979) and retroviral vectors (U.S. Pat. Nos. 5,624,820, 5,693,508 and 5,674,703 and WIPO publications WO 92/05266 and WO 92/14829).

For therapeutic use, agents of the invention (including nucleic acids encoding peptides) can be formulated with a pharmaceutically acceptable carrier at an appropriate dose. Such pharmaceutical compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically acceptable carrier, composition or vehicle, such as a liquid or solid filler, diluent, excipient, or solvent encapsulating material, is involved in carrying or transporting the subject agent from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The peptide, derivative or peptidomimetic of the invention can be used alone or used in combination with one or more other treatments for cardiovascular, thrombotic or hematologic diseases or disorders. In some embodiments, a peptide, derivative or peptidomimetic is administered in combination with another useful compositions or drug, such as an anti-inflammatory agent, an immunosuppressant, an antiviral agent, or the like. More specific examples include corticosteroids, aspirin, clopidogrel. In another embodiment, a peptide, derivative or peptidomimetic aptamer is used in combination with non-drug therapies or treatments, such as plasma exchange and PCI. In general, the currently available dosage forms of the known therapeutic agents and the uses of non-drug therapies for use in such combinations will be suitable.

"Combination therapy" (or "co-therapy") includes the administration of a peptide, derivative or peptidomimetic and at least a second agent or treatment as part of a specific treatment regimen intended to provide the beneficial effect from the co-action of these therapeutic agents or treatments. The beneficial effect of the combination includes, but is not limited to, pharmacokinetic or pharmacodynamic co-action resulting from the combination of therapeutic agent or treatments. Administration of these therapeutic agents or treatments in combination typically is carried out over a defined time period (usually minutes, hours, days or weeks depending upon the combination selected).

Combination therapy is intended to embrace administration of the therapeutic agents or treatments in a sequential manner. That is, wherein each therapeutic agent or treatment is administered at a different time, as well as administration of these therapeutic agents or treatments, or at least two of the therapeutic agents or treatments, in a substantially simultaneous manner. Substantially simultaneous administration can be accomplished, for example, by administering to the subject a single injection having a fixed ratio of each therapeutic agent or in multiple, single injections for each of the therapeutic agents.

Sequential or substantially simultaneous administration of each therapeutic agent or treatment can be effected by any appropriate route including, but not limited to, topical routes, oral routes, intravenous routes, subcutaneous, intramuscular routes, and direct absorption through mucous membrane tissues. The therapeutic agents or treatments can be administered by the same route or by different routes. For example, a first therapeutic agent or treatment of the combination selected may be administered by injection while the other therapeutic agents or treatments of the combination may be administered subcutaneously. Alternatively, for example, all therapeutic agents or treatments may be administered subcutaneously or all therapeutic agents or treatments may be administered by injection. The sequence in which the therapeutic agents or treatments are administered is not critical unless noted otherwise.

The invention is described in greater detail by the following non-limiting examples.

Example 1: Material and Methods

Endothelial Cells and Molecular Reagents.

Human umbilical vein endothelial cells (HUVECS), endothelial growth medium (EBM-2), and media supplements were purchased from Lonza (Walkersville, Md.). Human α-thrombin was obtained from Enzyme Research Laboratories (South Bend, Ind.). SIGENOME SMART-POOL and individual siRNA oligonucleotides were from Dharmacon Research Inc. (Lafayette, Colo.). Negative control, scrambled siRNA was from QIAGEN (Valencia, Calif.). siRNA transfection reagent was from Santa Cruz Technologies (Santa Cruz, Calif.). vWF secretion was measured with an enzyme-linked immunosorbant assay (ELISA) kit (Abnova, Taiwan) according to manufacturer's instructions. Murine vWF antigen was measured by ELISA using rabbit polyclonal anti-vWF antibody to capture antigen (Santa Cruz Biotechnology Inc.). Goat anti-rabbit vWF biotinylated polyclonal antibody was detected using streptavidin-peroxidase conjugate (Abnova, Taiwan). Commercially available antibodies were from Santa Cruz Biotechnology, Inc. Mouse monoclonal antibodies against guanine nucleotide G protein α (GNA) subunits GNA12, GNA13 and GNAq/11 were generated by the Laboratory for Systems Biology and Medicine, University of Tokyo, Japan as previously described (Hino, et al. (2012) *Nature* 482:237-240). Purified human vWF, GFP-tagged GNA12$^{WT}$, GFP-tagged constitutively active GNA12$^{Q229L}$ mutant, and Myc-tagged GNA12-Q229L 'NAAIRS' were obtained by conventional methods (Delaney, et al. (2012) supra). HUVEC were transfected with GNA12 constructs or vector alone by NUCLEOFECTION (Amaxa Inc.; Gaithersburg, Md.) according to manufacturer's instructions. PAR1 agonist peptide (Thr-Phe-Leu-Leu-Arg; SEQ ID NO:3) was synthesized at University of Illinois at Chicago.

Mice.

Wild-type (WT) mice were purchased from Harlan Laboratories Inc. (Madison, Wis.). Tie2-CreER$^{T2}$GNA12$^{-/-}$; GNA13$^{flox/flox}$ tamoxifen-inducible tie2-CreER$^{T2}$; GNA12$^{-/-}$; GNA13$^{flox/flox}$ (global G12$^{-/-}$ and endothelial cell-specific G13$^{-/-}$ double knockout (dKO)), tie2-CreER$^{T2}$ GNAq$^{flox/flox}$; GNA11$^{-/-}$ dKO, and tamoxifen-induced tie2-CreER$^{T2}$ GNAq$^{-/-}$; GNA11$^{flox/flox-/-}$ (global Gq$^{-/-}$ and endothelial cell-specific G11$^{-/-}$ dKO) breeding stock were as described (Korhonen, et al. (2009) *J. Exp. Med.* 206(2): 411-420; Moers, et al. (2003) *Nat. Med.* 9(11):1418-1422).

Cell Culture and siRNA Transfection.

HUVEC were cultured on 0.1% gelatin-coated plates. Early passage HUVEC (passage 2-5) were transfected with a pool of four siRNA oligonucleotides directed against GNA12, GNA13, GNAq, RhoA, αSNAP, or control RNA (QIAGEN), harvested 48 hours later, and analyzed by western blot. Protein levels were normalized to Hsp90 or tubulin loading controls.

Cultured Human Endothelial Cell vWF Secretion Assay and ELISA.

vWF secretion assay was as previously described (Lui-Roberts, et al. (2005) *J. Cell Biol.* 170:627-636). In brief, 48 hours after transfection, endothelial cells were serum-deprived for 4 hours, washed, and incubated with fresh serum-free medium in presence or absence of 25 nM thrombin, A23187 (a calcium ionophore), or culture medium alone (vehicle control). Cell culture media was collected at various time points after agonist stimulation and centrifuged for 10 minutes at 13,000×g to remove cell debris. Supernatants were assayed for vWF content by ELISA. Cells were lysed to determine total vWF secreted per 10$^6$ cells. The concentration of vWF was expressed as mIU/ml/10$^6$ cells by relating the absorbance at 450 nm to a vWF standard curve. The lower limit of detection for this assay was 0.1 mIU/mL. To prevent potential differences in releasable vWF, the same batch of HUVEC was used for all experiments, and control and siRNA treated cells were assessed at equivalent cell densities.

Tail Bleeding Time and Blood Loss.

Mice were anaesthetized using 100 mg/kg ketamine and 5 mg/kg xylazine. Once unresponsive to tail pinch, 3-5 mm of the end of the tail was removed with a scalpel, the tail was immersed in 0.9% saline solution (37° C.), and time required for bleeding to stop was recorded (n=10 male mice/group, age 8-12 weeks) according to established methods (Lu, et al. (2011) *Cell Res.* 21:530-545). If no cessation of bleeding occurred after 30 minutes, the tail was cauterized with a cautery pencil and 30 minutes was recorded as the bleeding time. Blood loss during the bleeding time experiments was expressed as the accumulated amount of hemoglobin (Hb) bled into the container with phosphate-buffer saline in which tails were immersed. Hb (mg Hb/mL saline) was analyzed over the period of the experiment, using Hemocue HB201+ (Hemocue; Cypress, Calif.). Mice were allowed to recover in a clean cage. Human plasma-derived vWF, diluted in sterile saline solution to 25 µg/mL, was infused into GNA12$^{-/-}$ mice by i.v. administration. Control mice were administrated saline (vehicle).

Blood Collection.

Mice were anaesthetized by ketamine/xylazine as above and ventilated according to conventional methods. Blood was collected by inferior vena cava puncture. Plasma was prepared from citrated blood samples via centrifugation at 3,000×g for 15 minutes at room temperature and stored at −80° C. until vWF measurement by ELISA. The anesthetized mouse was then euthanized for lung tissue collection as described below.

Ex-Vivo Lung Perfusion, Sample Collection, Preparation and Storage.

Anesthetized GNA12$^{-/-}$, GNA12$^{-/-}$/EC GNA13$^{-/-}$, GNAq$^{-/-}$, and GNAq$^{-/-}$/EC GNA11$^{-/-}$ mice were instrumented with a tracheal tube, cannulated via pulmonary artery, and perfused with warmed Krebs buffer at a rate of 1 ml/min for 5 minutes to remove residual blood constituents followed by treatment for 20 minutes with 2 ml recirculating Krebs buffer to assess constitutive vWF secretion. To assess thrombin-induced endothelial cell secretion of vWF, 100 nM PAR1-specific peptide (Thr-Phe-Leu-Leu-Arg; SEQ ID NO:3) was added to the recirculating buffer. vWF release (mU/ml perfusate) measured by ELISA was used to assess endothelial-specific hemostatic and thrombotic vWF levels in WT and G protein-deficient mice, which were compared to cultured human endothelial cell vWF release. Following lung perfusion, lungs were minced and snap-frozen in liquid nitrogen for subsequent determination of whole lung extract vWF levels.

Mouse Whole Lung Homogenate.

Ventilated and cleared lungs were harvested and homogenized using a POLYTRON tissue homogenizer in pre-chilled lysis buffer (1M Tris-HCl pH 7.5, 5M NaCl, 10% TRITON X-100, 10% desoxycholic acid, 10% SDS) in presence of protease inhibitor cocktail (Sigma) and phenyl-methylsulfonyl fluoride (Pierce) and then incubated on ice for 30 minutes to allow tissue dissociation. Supernatants were decanted from the insoluble material via centrifugation at 13,000×g for 20 minutes at 40° C., transferred into new EPPENDORF tubes, and stored at −80° C.

vWF Measurements.

Mouse samples were collected and vWF level was measured by sandwich ELISA (Lu, et al. (2011) supra). One unit of vWF was defined as the amount present in 1 ml of mouse pooled normal plasma.

Fluorescence Intravital Microscopy.

Real-time intravital microscopy of cremaster muscle arterioles was performed according to established methods. Briefly, male WT and GNA12$^{-/-}$ mice (8 weeks old) were anesthetized by an intraperitoneal injection of ketamine (125 mg/kg) and xylazine (25 mg/kg). A tracheal tube was inserted and the mouse was placed on a thermo-controlled blanket. After incision of the scrotum, the cremaster muscle was exteriorized onto an intravital microscopy tray. The muscle preparation was superfused with thermo-controlled (37° C.) and aerated (95% N$_2$, 5% CO$_2$) bicarbonate-buffered saline throughout the experiment. The cremaster muscle arteriolar wall was injured by micropoint laser ablation using a Micropoint Laser System (Photonics Instruments; South Windsor, Conn.). The developing mouse platelet thrombus was monitored by infusion of DYLIGHT 649-conjugated anti-mouse CD42c antibody (Emfret Analytics, 0.05 µg/g body weight) through a cannulus placed in the jugular vein. Multiple thrombi were generated in each mouse, with each new ablation being made upstream of the earlier one to avoid confounding effects of previous thrombi on the newly forming one. Fluorescence and bright field images were recorded using an Olympus BX61 W microscope with a 60×/1.0 NA water immersion objective and a high speed camera (Hamamatsu C9300) through an intensifier (Video Scope International). Data were collected for 5 minutes following vessel wall injury and analyzed using SLIDEBOOK v5.0 (Intelligent Imaging Innovations; Denver, Colo.).

Platelet Preparations.

Human blood was drawn under steady conditions from non-medicated healthy donors according to a standard IRB-approved protocol upon informed consent. Washed platelets were resuspended in Tyrode's buffer in a volume equivalent to the original plasma volume.

Flow-Based Platelet Adhesion Assay.

To functionally assess vWF secretion, formation of strings of platelets aligned on vWF secreted from HUVEC exposed to physiological flow conditions was imaged. Following shear treatment ($600\ s^{-1}$), HUVECs were fixed in 4% PFA and stained with rabbit anti-human vWF and mouse anti-human GpIb antibodies and with ALEXAFLUOR 555 goat anti-mouse and ALEXAFLUOR 488 goat anti-rabbit secondary antibodies. The number of platelets adherent per vWF filament and the length of the vWF string was measured using Image J software.

Immunostaining.

Endothelial cells cultured on gelatin-coated glass bottom dishes were fixed with 4% paraformaldehyde, permeabilized with 0.1% TRITON X-100, blocked with 5% goat serum for 1 hour, and subsequently incubated with rabbit polyclonal antibody directed against vWF (0.5 µg/ml) or contral IgG overnight at 4° C. Coverslips were washed 3× with phosphate-buffered saline and incubated for 30 minutes at room temperature in the dark with ALEXAFLUOR 555 goat anti-mouse and ALEXAFLUOR 488-labeled goat anti-rabbit secondary antibody. Coverslips were washed with phosphate-buffered saline and embedded in mounting media (VECTASHIELD). Confocal microscopy was performed using a ZEISS LSM 510 Meta microscope (Carl Zeiss MicroImaging, Inc.) equipped with 488 nm and 543 nm excitation lasers and pinhole set to achieve 1 Airy unit.

Quantification of Number of WPBs in Thrombin-Stimulated ECs Versus Control.

Weibel-Palade Bodies (WPBs) were identified based on vWF immunofluorescence staining, size (approximately 3 µm long and 0.3 µm wide), and shape (elongated organelles). For determination of the number of WPBs per cell, binary confocal microscopy images had a threshold and an Image J plug-in was used to analyze particle density and intensity/cell. The number of WPBs per cell was counted (n=10-30) and the average fluorescence intensity per WPB/cell determined.

GST-Pulldown.

GST-αSNAP fusion protein and control GST were expressed in bacteria and purified using glutathione-agarose beads. Purified proteins were analyzed by SDS-PAGE and COOMASSIE staining, and protein concentration was estimated by Bradford assay. Positive control Myc-tagged activated GNA12 and GNA12 'NAAIRS' cassette, constitutively active GNA12 lacking the αSNAP Binding Domain (ΔSBD) or constitutively active GNA12 in which 6 amino acids at the N-terminus of GNA12 were substituted (ΔNI2) were expressed at comparable levels in HEK 293A cells. Equimolar amounts of GST-αSNAP or GST were incubated with cell lysates and bound protein was detected by western blot using anti-Myc antibody.

Statistical Analysis.

Data are mean±SEM. Statistical significance was assessed by one-way ANOVA with Bonferoni post hoc testing. P less than 0.05 was considered significant.

Example 2: Blood Levels of vWF in Gα12/13 and Gαq/11 Deficient Mice

To assess the physiologic role of G protein signaling in the production of circulating vWF, plasma levels of vWF were measured in Cre-Gα13$^{flox/flox}$; Gα12$^{-/-}$ and Cre-Gαq$^{flox/flox}$; Gα11$^{-/-}$ mice (Korhonen, et al. (2009) supra), with or without tamoxifen (TX) treatment to induce endothelial Cre activation and resultant Gαq gene deletion in global Gα11$^{-/-}$ or Gα13 deletion in global Gα12$^{-/-}$ mice. To exclude effects of TX per se on plasma levels of vWF, TX (1 mg per day for 5 days) was administered to WT mice (n=2) and blood was collected from the tail vein on day 1 (just before the first TX injection), 3, 7, 10 and 14. On day 3, a small transient increase in plasma vWF level was observed, and then plasma vWF level normalized on day 7, 10, and 14 (the day of the experimental procedure).

Plasma from Gα12$^{-/-}$ and EC-Gα13$^{-/-}$; Gα12$^{-/-}$ mice exhibited significantly reduced plasma levels of vWF as compared to WT, Gα11$^{-/-}$, and EC-Gαq$^{-/-}$; Gα11$^{-/-}$ mice. However, there was no significant difference in the percentage of low, intermediate, or high-molecular weight vWF multimers in Gα12$^{-/-}$ plasma indicating vWF secretion rather than vWF packaging or processing was defective in absence of Gα12. These data indicate that Gα12 may play an important role in maintaining basal blood levels of vWF.

Example 3: Role of Gα12 and Gαq/11 in Constitutive Vs. Evoked Endothelial vWF Secretion To address the role of G protein α subunits in constitutive (basal, spontaneous) vs. PAR-1-mediated vWF secretion from endothelial cells, vWF was measured in the ex vivo isolated buffer-perfused mouse lung (IPML). Lung preparations were used to exclude platelets as a source of vWF and also hepatic stellate cells as contributors of proteases that cleave ultra large vWF strings (Lenting, et al. (2012) supra). Ventilated WT, Gα12$^{-/-}$, and EC-Gαq$^{-/-}$; Gα11$^{-/-}$ mouse lungs were cannulated and perfused with warmed recirculating RPMI media via pulmonary artery and left atrial catheters in situ. To assess basal vWF secretion, precleared blood-free lungs were perfused for 15 minutes with 5 ml of 37° C. recirculating RPMI media (approximately the same volume as the normal mouse blood volume). Samples of the recirculating buffer were collected at 5 minute intervals over a period of 30 minutes and vWF (mU/ml perfusate) was measured by ELISA.

vWF was detectable in the lung perfusate immediately after initiating perfusion with fresh media (116.2±7.7 mU/mL at the 5 minute time point in WT mice, 106.6±13.6 in cEC-Gαq$^{-/-}$; 11$^{-/-}$ mice, but only 6.2±0.8 mU/mL in Gα12$^{-/-}$ mice). The accumulation of vWF in recirculating lung perfusate over time described a straight line in WT mice (secretion rate=2.5 mU/mL/min). Intriguingly, baseline vWF values were significantly lower in Gα12$^{-/-}$ mouse lungs (secretion rate=0.6±0.03 mU/mL/min).

To assess the mechanism of thrombin-induced vWF release from ECs via PAR-1 activation, the PAR-1-specific synthetic peptide Thr-Phe-Leu-Leu-Arg (SEQ ID NO:3)

was used to stimulate lung ECs. Addition of 30 μM Thr-Phe-Leu-Leu-Arg (SEQ ID NO:3) to the recirculating lung perfusate sharply increased vWF level in WT mice which peaked after 10-15 minutes and remained constant for up to 1 hour. The initial slope of the vWF secretion curve was used to estimate the rate of vWF release following addition of Thr-Phe-Leu-Leu-Arg (SEQ ID NO:3), which was approximately 25 mU/mL/min in WT mouse lungs. In $G\alpha12^{-/-}$ mouse lungs, Thr-Phe-Leu-Leu-Arg (SEQ ID NO:3)-induced vWF secretion was significantly reduced (3 mU/mL/min). Under these same conditions, basal vWF secretion in the pulmonary circulation of EC-$G\alpha q^{-/-}$; $G\alpha 11^{-/-}$ lungs was not different from that observed in WT mice, although Thr-Phe-Leu-Leu-Arg (SEQ ID NO:3)-induced vWF release was reduced by approximately 40%. Consistent with these findings, equivalent vWF immunoreactivity was observed in blood-free homogenates of non-stimulated WT, $G\alpha 12^{-/-}$, and EC-$G\alpha q^{-/-}$; $G\alpha 11^{-/-}$ mouse lungs. However, significantly greater vWF remained in $G\alpha 12^{-/-}$ and EC-$G\alpha q^{-/-}$; $G\alpha 11^{-/-}$ lungs after Thr-Phe-Leu-Leu-Arg (SEQ ID NO:3) stimulation indicating that vWF is being made although thrombin-evoked secretion from lung vascular endothelium is significantly reduced in absence of $G\alpha 12$ or $G\alpha q/11$. The majority of vWF in $G\alpha 12^{-/-}$ mouse lungs was retained in the lung (not secreted) whereas in EC-$G\alpha q^{-/-}$; $G\alpha 11^{-/-}$ mouse lungs, basal secretion was normal but TFLLR-evoked EC-derived vWF secretion was significantly reduced. The presence of EC WPB vWF in en face descending aorta and paraffin-embedded lung sections was verified by immunostaining and confocal microscopy. WT, $G\alpha 12^{-/-}$, and $G\alpha 11^{-/-}$ tissues stained positive for vWF consistent with there being equivalent vWF synthesis and storage in WPBs in WT, $G\alpha 12^{-/-}$, and $G\alpha 11^{-/-}$ mice.

Example 4: Regulation of Hemostasis and Thrombosis by $G\alpha 12$

Using megakaryocyte-restricted-$G\alpha 12/13$ double knock-out mice, it has been observed that $G\alpha 13$-dependent signaling in platelets is important for hemostasis and thrombosis (Moers, et al. (2003) *Nat. Med.* 9(11):1418-1422). However, the molecular mechanisms and functional significance of endothelial cell $G\alpha 12$ and $G\alpha 13$ in primary hemostasis were not assessed. As a direct measurement of primary hemostasis, blood loss was determined after tail-snip in anesthetized EC-$G\alpha 13^{-/-}$; $G\alpha 12^{-/-}$ vs. WT mice (n=3 male mice/group, age 8 weeks) as previously described (Shi, et al. (2012) *Haemophilia* 18(4):639-646). Hb accumulation from the cut tail immersed in saline solution was measured every 5 minutes for 15 minutes. The induced hemorrhagic event was significantly prolonged in EC-$G\alpha 13^{-/-}$; $G\alpha 12^{-/-}$ mice compared to WT mice. In addition, EC-$G\alpha 13^{-/-}$; $G\alpha 12^{-/-}$ mice were prone to spontaneous hemorrhagic incidents in the abdominal cavity and recurrence of bleeding after stoppage. Consistent with the primary hemostasis defect being due to low plasma level of vWF, hemostasis was corrected by i.v. administration of purified human plasma-derived vWF (2 μg/g BW).

Mice with $G\alpha 12$ deficiency exhibited low vWF levels in blood-free lung vascular perfusates and elevated vWF level in blood-free lung homogenates both before as well as after PAR-1 stimulation. Thus, $G\alpha 12$ may be important for maintaining basal levels of circulating vWF required for platelet thrombus formation. To investigate the role of $G\alpha 12$ in platelet thrombus formation in vivo, real-time fluorescence intravital microscopy was performed in anesthetized mice. Following arteriolar wall injury induced by micropoint laser ablation, platelets were monitored by Dylight 649-conjugated anti-mouse CD42c antibody. In both WT and $G\alpha 12^{-/-}$ mice, platelet thrombus formation was initiated at the site of arteriolar injury. However, the platelet thrombus did not grow at the injury site in $G\alpha 12^{-/-}$ mice as compared with WT mice. From these results, it was concluded that $G\alpha 12$-dependent EC vWF secretion is required for hemostasis and thrombosis and focused on this mechanism in comparison to EC $G\alpha q$ signaling in subsequent studies.

Example 5: Potentiation of $G\alpha 12$-Dependent Basal EC-vWF Release by Thrombin-Stimulated $G\alpha q/G\alpha 11$- and $G\alpha 12$-Regulated EC-vWF Secretion The role of G protein signaling in basal vs. PAR1-stimulated vWF secretion from confluent, low passage, and serum-deprived HUVECs and HPAECs was subsequently determined. Using a siRNA approach, G protein α subunits $G\alpha q$, $G\alpha 12$ and $G\alpha 13$ were depleted from HUVEC and HPAEC. In order to quantify vWF release in response to thrombin stimulation, two complementary protocols were established: 1) secretion/ELISA for quantification of vWF release from EC monolayers and 2) fluorescence microscopy for visualization/quantification of WPBs in individual cells, which provide a quantitative measure of vWF exocytosis/secretion kinetics from endothelial cells both basally and upon PAR1 activation.

To demonstrate that $G\alpha 12$ signaling in endothelial cells regulates vWF secretion, HUVECs and HPAECs were transfected with control or $G\alpha 12$ siRNA and 48 hours later, cells were serum starved for a minimum of 4 hours and then stimulated with 25 nM α-thrombin for up to 1 hour. After $G\alpha 12$ siRNA treatment, the level of $G\alpha 12$ expression decreased to a level not detected by western blotting but had no effect on $G\alpha q$ or $G\alpha 13$ expression. Consistent with the knockout mouse studies, $G\alpha 12$ siRNA significantly reduced basal as well as thrombin-induced vWF secretion from HUVEC as well as HPAEC. Following the transfection of $G\alpha 13$ siRNA, which depleted $G\alpha 13$ but not $G\alpha 12$ or $G\alpha q$ protein; however, no significant effect on basal or thrombin-induced vWF secretion was observed. These data indicate that $G\alpha 12$ but not $G\alpha 13$ mediates EC-specific basal as well as thrombin-induced vWF release from cultured HUVEC and HPAEC.

The involvement of $G\alpha q$ in the regulation of the vWF secretory pathway was subsequently investigated. $G\alpha q$ siRNA resulted in nearly complete $G\alpha q$ depletion while $G\alpha 12$ protein level remained unchanged. Following $G\alpha q$ depletion, the amount of vWF released upon thrombin stimulation was reduced by 40% in HUVEC and 60% in HPAEC whereas basal vWF secretion was not affected. These data indicate that $G\alpha q$ is important in thrombin-evoked EC vWF secretion.

Example 6: Role of NSF/αSNAP, p115RhoGEF and RhoA in Basal Vs. Thrombin-Induced vWF Release N-Ethylmaleimide (NEM) is a well-known inhibitor of exocytosis in endothelial cells (Niles & Malik (1999) *J. Membr. Biol.* 167(1):85-101). Consistent with the notion that WPB exocytosis requires NSF/α-SNAP (Matsushita, et al. (2003) supra), addition of 1 mM NEM to the recirculating lung perfusion system for 1 minute abolished vWF secretion. To explore the role of α-SNAP in constitutive and thrombin- or calcium ionophore-induced vWF release from human endothelial cells, siRNA was used to deplete α-SNAP from HUVEC and then vWF was measured by ELISA as above. Cell lysates were also saved for western blot analysis. It was observed that α-SNAP depletion completely blocked basal and thrombin- as well as calcium ionophore-induced vWF secretion. These data demonstrate that α-SNAP is required for all forms of vWF secretion.

In p115 RhoGEF and RhoA siRNA-depleted HUVECs, thrombin-induced vWF secretion was reduced by 20-40% although basal vWF secretion was not affected. Thus, Gα12-mediated basal vWF secretion occurs independently of the Rho pathway whereas receptor-mediated Gα12 and/or Gαq/11 signaling enhances vWF secretion via p115 RhoGEF and RhoA signaling.

Example 7: siRNA-Mediated Gα12 Depletion Blocks Thrombin-Induced WPB Exocytosis To distinguish whether the inhibitory effect of Gα12 depletion on vWF secretion is due to inhibition of vWF secretion as opposed to impaired vWF production or storage, vWF immunostaining and confocal microscopy of control siRNA and Gα12 siRNA-treated HUVECs was performed in presence or absence of thrombin stimulation. This analysis indicated that unstimulated HUVEC transfected with control or Gα12 siRNA exhibited vWF-staining patterns consistent with localization in WPBs, and siRNA-downregulation of Gα12 did not impair synthesis or packaging of vWF. Quantification of vWF staining and the number of WPBs per cell revealed that >80% of resting cells contained multiple WPBs/cell. Interestingly, image analysis revealed greater intracellular vWF staining in Gα12 siRNA-treated HUVECs compared with control siRNA-treated cells in absence of thrombin stimulation. Thirty minutes after thrombin treatment of control cells, a >80% decrease in intracellular vWF staining was observed, which was uniform throughout the endothelial cell monolayer suggesting thrombin-induced WPB exocytosis of vWF. However, total intracellular vWF staining as well as the number of vWF positive fluorescent structures (i.e., WPBs) per cell observed following thrombin stimulation were significantly greater in Gα12-depleted HUVECs compared with control siRNA-treated cells indicating thrombin-induced vWF secretion via WPB exocytosis was prevented in absence of Gα12.

Example 8: Depletion of Endothelial Cell Gα12 Impairs vWF-Dependent Platelet Adhesion Platelet adhesion is one of the earliest responses to vascular injury and is directly influenced by blood flow (Brill, et al. (2011) *Blood* 117(4):1400-1407). To elucidate the role of Gα12 signaling in vWF secretion and thrombosis evoked by shear stress, a functional flow-based assay was used and platelet adhesion along secreted strands of vWF was imaged (Yin, et al. (2008) *Blood* 111(2):658-665). A shear rate of 600 s$^{-1}$ (~6 dynes/cm$^2$) induced by a cone-plate rheometer was used to mimic physiologic arterial or arteriolar wall shear forces (Ruggeri, et al. (1983) *J. Clin. Invest.* 72(1):1-12) and promote the formation of vWF strings emanating from cultured ECs. Control siRNA or Gα12 siRNA-treated HUVECs were exposed to uniform and constant shear in presence or absence of washed platelets. Platelet adhesion/alignment on vWF 'strings' was assessed 5 minutes after shear initiation by fixation with 2% paraformaldehyde and immunostaining with anti-vWF and anti-Gp1b antibodies. Representative confocal images and summarized data indicate that depletion of Gα12 impaired shear-induced platelet adhesion along vWF strings. Therefore, EC vWF secretion and subsequent formation of vWF filaments to which platelets adhere requires EC Gα12.

Example 9: Activated Gα12 Stimulates WPB Exocytosis from HUVECs

To elucidate the role of Gα12 in WPBs exocytosis, HUVEC were transfected with constitutively-active GFP-tagged Gα12$^{Q229L}$ mutant, GFP-tagged Gα12$^{WT}$, or GFP alone, and then confocal images of vWF immunostaining were quantified. Transfection with GFP alone did not affect the distribution or number of WPBs per cell. Upon 25 nM thrombin stimulation for 15 minutes, the majority (80%) of GFP-positive control cells showed reduced vWF positive WPBs. In non-stimulated cells expressing Gα12$^{WT}$ or constitutively active Gα12$^{Q229L}$ mutant (10-30 cells per experiment, n=4), less intracellular vWF staining (p<0.05 vs. GFP alone) was observed indicating that the WPBs had been depleted of vWF due to Gα12-dependent exocytosis.

Example 10: Gα12 Modulation of α-SNAP Regulates vWF Exocytosis

Figure 1:
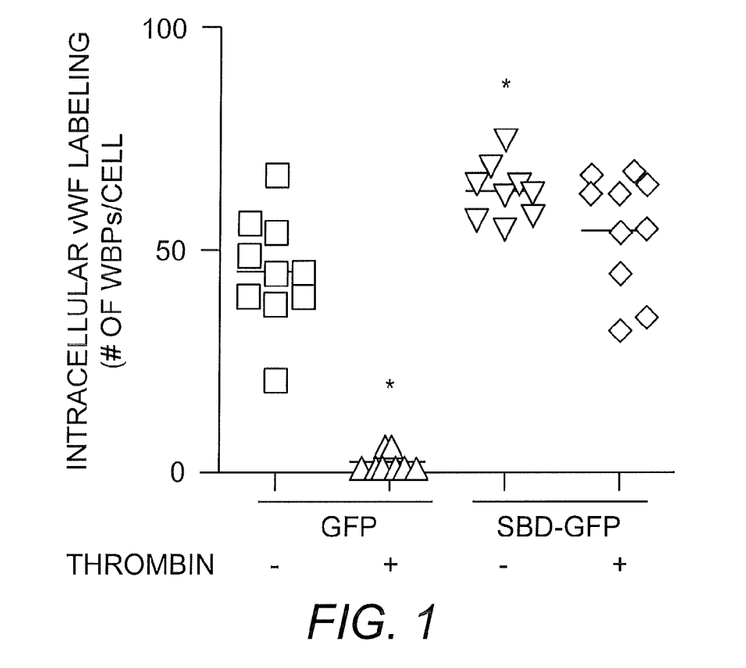
FIG. 1 shows the dominant-negative effect of GFP-tagged-SBD on basal and thrombin-induced vWF secretion in HUVEC. *=p<0.05 vs. unstimulated; n=7-15 cells/group; red line=median value.

It was observed that α-SNAP siRNA blocks basal, thrombin-evoked, and Ca$^{2+}$ ionophore-induced secretion of vWF indicating that α-SNAP-mediated fusion of WPBs is required for vWF secretion. The role of Gα12/αSNAP interactions in regulation of vWF secretion was analyzed using a two-step experimental approach. First, a library of Gα12-substitution mutants (Meigs, et al. (2005) *J. Biol. Chem.* 280(18):18049-18055) was used, in which the primary sequence of Gα12 was replaced with the Asn-Ala-Ala-Ile-Arg-Ser (SEQ ID NO:5; NAAIRS cassette) to assess domain-specific in vitro binding of Myc-tagged Gα12$^{Q229L}$ with or without 'NAAIRS' substitution of N-terminal amino acids 4-9 (ΔN4-9) or 10-15 (ΔN10-15) to GST-αSNAP. It was observed that six residues in the primary sequence of the Gα12 (Arg-Cys-Leu-Leu-Pro-Ala; SEQ ID NO:1) were required for Gα12 binding to α-SNAP, whereas ΔN4-9 mutant binding to α-SNAP was not significantly different from Gα12$^{QL}$. Secondly, to assess the role of Gα12 interaction with α-SNAP in vWF secretion, a GFP-tagged α-SNAP Binding Domain (aa 10-15) minigene (GFP-SBD) was constructed based on the identified Gα12•GST-αSNAP interaction. In unstimulated cells, vWF staining in GFP-SBD-expressing HUVECs was similar to control GFP-expressing cells. However, intracellular vWF staining was significantly reduced following thrombin-stimulation of control cells (expressing empty GFP vector) whereas vWF staining remained unchanged in GFP-SBD expressing cells (FIG. 1). These results indicate that the GFP-SBD minigene inhibited thrombin-induced WPB exocytosis in support of our thesis that Gα12 promotes vWF secretion from WPBs by directly interacting with α-SNAP.

Example 11: Inhibition of vWF Secretion by Myr-SBD Peptide

Figure 2:
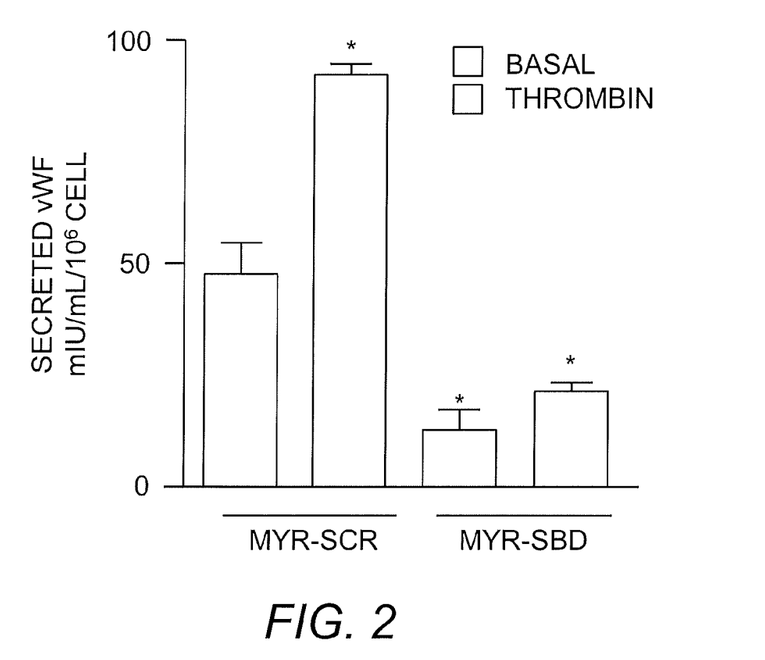
FIG. 2 shows that Myr-SBD peptide blocks basal and thrombin-induced VWF secretion. ELISA assay determination indicates Myr-SBD (Myr-SBD; Myr-Arg-Cys-Leu-Leu-Pro-Ala (SEQ ID NO:2) 1 µM) but not scrambled peptide (Myr-Cys-Arg-Ala-Leu-Pro-Leu (SEQ ID NO:4)) Myr blocks basal and thrombin-evoked vWF.
Figure 3A:
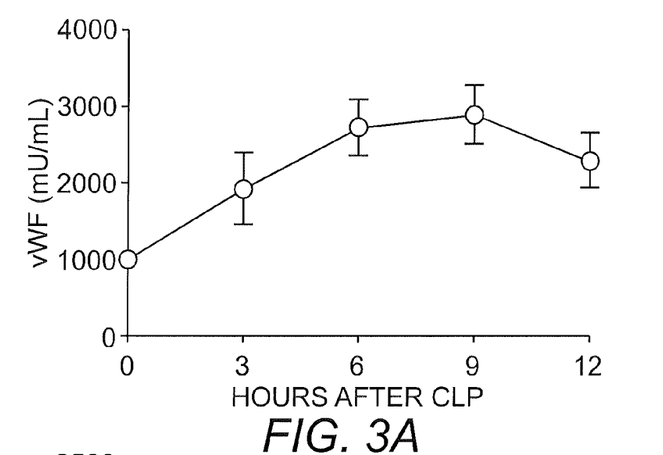
Figure 3B:
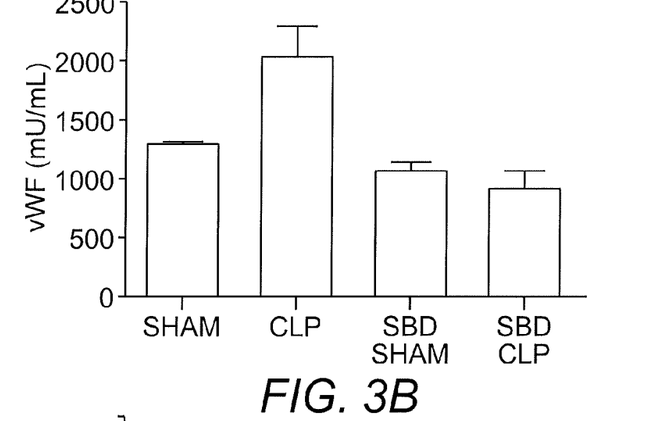
Figure 3C:
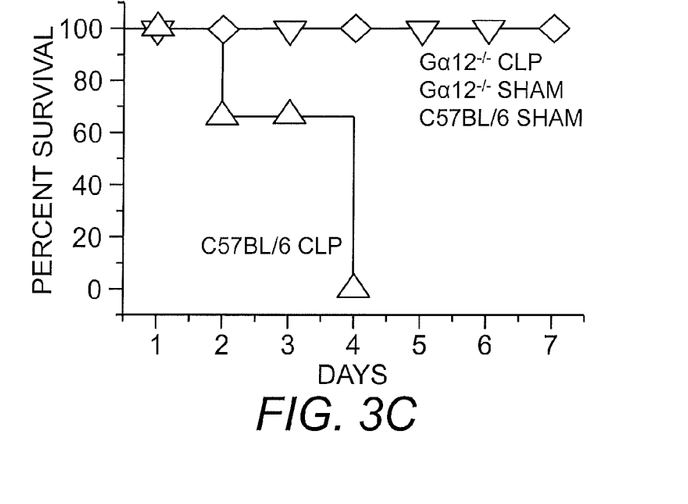

It was determined whether Gα12 interaction with αSNAP plays an important role in both basal and evoked VWF secretion from endothelial cell WPBs in vitro and in vivo. Myr-SBD peptide (1 μM; 1 hour pre-incubation) blocked both basal VWF secretion and that evoked by thrombin stimulation of HPAEC (FIG. 2). The effect of Gα12 and Myr-SBD on vWF secretion was assessed as was mortality associated with CLP/sepsis in rodent models. As shown in FIG. 3A, CLP-induced fulminant sepsis in WT Sprague-Dawley rats was associated with a two-fold increase in plasma vWF within 4 hours, reached maximum levels after 6-10 hours, and remained elevated above sham-operated control plasma levels at 12 hours. Importantly, reduced plasma vWF levels (FIG. 3B) were observed 24 hours after SHAM or CLP surgery in mice given 100 µl of 100 µM Myr-SBD (~5 µM) as compared to mice treated with Myr-Scrambled peptide. Consistent with the hypothesis that Gα12-dependent increase in vWF secretion during sepsis leads to poor outcome, 3/3 WT mice succumbed to sepsis in less than 96 hours (FIG. 3C) whereas 3/3 Gα12$^{-/-}$ mice known to have significantly reduced plasma VWF levels survived CLP-induced sepsis.

Example 12: Role of Myr-SBD in CLP-Induced vWF Secretion, Microvascular Thrombosis, and Mortality Associated with Sepsis Three different rodent models of sepsis are to assess the activity of Myr-SBD: LPS injection, CLP, and *E. coli* injection. The effects of Gα12/α-SNAP inhibitor Myr-SBD vs. scrambled control peptide (Myr-Scr) on vWF secretion, tail-snip blood loss, glomerular thrombosis, and mortality are determined. Intravascular injection of micellar myristoylated peptides (SBD vs Scr) is performed immediately following CLP or i.v. injections of LPS or *E. coli*, as well as 12 and 24 hours after challenge. Blood is collected at 12, 24, 48, 72, and 168 hour time points for measurement of vWF. Dose response studies (peptide blood levels of 0.01-10 µM at the time of injection) are conducted initially in the isolated perfused mouse lung to determine the minimally effective dose that is assessed in vivo. Blood levels of Myr-SBD and Myr-Scr peptides are estimated using 1-pyrenyldiazomethane (PDAM) labeled peptides by measuring fluorescence intensity (Abs 340 nm/emission 395 nm). The levels of PDAM-labeled peptides that accumulate in vascular endothelial cells are also estimated by measuring PDAM fluorescence in fresh-frozen lung sections using a confocal microscope with 350 nm laser excitation. Here, UV fluorescence is correlated with intracellular fluorescence intensity of vWF antibody staining (488 nm ex) in CD31 positive (568 nm ex) endothelial cells.

Results showing transient decreases in plasma vWF level following administration of Myr-SBD peptide are followed-up with studies in which animals are given multiple doses of Myr-SBD after sepsis challenge. Bleeding time, vWF, and platelet counts are measured daily, and plasma, lungs, and kidneys are collected for analysis of peptide levels, vWF concentration, and microvascular thrombosis. In these studies, the effects of micellar Myr-SBD vs. Scr are determined as well as the kinetics of Myr-SBD clearance. Determination of the role of Myr-SBD in basal vs. sepsis-evoked vWF secretion provides for a conclusion as to whether lowering vWF decreases microvascular thrombosis and mortality. Specificity of the Myr-SBD peptide is investigated using Gα12$^{-/-}$ mice. In addition, the effect of Myr-SBD vs. Myr-Scr on laser-induced microvascular thrombosis is directly assessed by intravital microscopy (Photonics Instruments). Here, the adhesion and aggregation of fluorescently-tagged platelets at the site of vascular injury are monitored in the presence and absence of Myr-SBD vs. Myr-Scr peptides.

Example 13: Analysis of Gα12/αSNAP-Dependent vWF Secretion In Vitro

Primary culture endothelial cells (HPAEC and MLEC) are used to determine the effect of Gα12/αSNAP inhibitor Myr-SBD on WPB trafficking, fusion, and exocytosis of vWF. vWF exocytosis is estimated in the presence and absence of increasing concentration of Myr-SBD vs. Myr-Scr as well as the Gα13 inhibitor peptide mP$_6$ following PAR-1 activation. GFP-vWF expressed in ECs is imaged in live cells by spinning disc confocal microscopy (Perkin Elmer Ultraview), where vWF exocytosis in the presence and absence of increasing concentration of Myr-SBD vs. Myr-mP$_6$ peptides and PAR-1 activation is defined as a decrease in vWF fluorescence intensity relative to the total number of GFP-vWF+ fluorescent objects. In this context, vWF secretion is verified by ELISA and the specificity of Myr-SBD and mP$_6$ peptides determined in Gα12, Gα13, and αSNAP siRNA treated cells. Expression of pcDNA3.1Gα12QL vs. Gα13QL full length constructs and deletion mutants with SBD ($\Delta N_{10-15}$) and switch region I ($\Delta$p115RhoGEG binding domain) are used to determine the relative role of Gα12/αSNAP interaction vs. RhoA-dependent actin polymerization in basal vs. evoked WPB exocytosis and specificity of Myr-SBD peptide-mediated inhibition of vWF secretion. Flow-dependent adhesion of platelets on vWF strings with and without stimulation by thrombin, LPS, or live *E. coli* are also assessed. The subcellular localization of YFP-Gα12 and CFP-αSNAP are analyzed in live cells and those fixed and stained for vWF and actin (labeled by RFP, TEXAS RED or far-red fluorophore) to determine whether Gα12 and αSNAP co-localize on WPBs and whether this interaction is disrupted by Myr-SBD. Velocity particle tracking software is used to quantify WPB movement and vWF exocytosis. Using immunoprecipitation, immunoblot, and in vitro enzyme activity assays, the role of Gα12/αSNAP interaction in mediating NSF activation and vWF secretion is assessed. From these in vitro studies, significant insight is gained as to the role of Gα12 as a catalyst of αSNAP-dependent NSF activation, the rate-limiting step in WPB exocytosis, which allows for an assessment of the mechanism of Myr-SBD mediated inhibition of vWF secretion in vivo. These studies also address the specificity of Myr-SBD-mediated inhibition of endogenous Gα12/αSNAP interactions critical for vWF release during pro-thrombotic and pro-inflammatory conditions observed in sepsis.

What is claimed is:

1. A peptide comprising the sequence Arg-Cys-Leu-Leu-Pro-Ala (SEQ ID NO:1), or a derivative or peptidomimetic thereof, wherein said peptide is less than 45 amino acid residues in length.

2. The peptide of claim 1, wherein the derivative comprises a post-translation modification selected from the group consisting of acetylation, amidation, formylation, hydroxylation, methylation, myristoylation, phosphorylation, sulfatation, glycosylation, and lipidation.

3. The peptide of claim 1, wherein said peptide is 6 to 15 amino acid residues in length.

4. A pharmaceutical composition comprising the peptide, derivative or peptidomimetic of claim 1 in admixture with a pharmaceutically acceptable carrier.

5. A method of inhibiting thrombin-induced von Willebrand Factor secretion comprising contacting an endothelial cell with the peptide of claim 1 thereby inhibiting thrombin-induced von Willebrand Factor secretion.

6. A method for preventing or treating thrombosis in a subject comprising administering to a subject in need of treatment the pharmaceutical composition of claim 4, thereby preventing or treating thrombosis in the subject.

* * * * *

SEQUENCE LISTING

<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

```
<400> SEQUENCE: 1

Arg Cys Leu Leu Pro Ala
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: myristoylated

<400> SEQUENCE: 2

Arg Cys Leu Leu Pro Ala
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide

<400> SEQUENCE: 3

Thr Phe Leu Leu Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: myristoylated

<400> SEQUENCE: 4

Cys Arg Ala Leu Pro Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Asn Ala Ala Ile Arg Ser
1               5
```